United States Patent
Friese et al.

(10) Patent No.: US 6,408,680 B2
(45) Date of Patent: *Jun. 25, 2002

(54) SENSOR AND METHOD FOR THE MANUFACTURE

(75) Inventors: Karl-Hermann Friese; Heinz Geier, both of Leonberg; Helmut Weyl, Schwieberdingen; Hans-Martin Wiedenmann, Stuttgart, all of (DE)

(73) Assignee: Robert Bosch GmbH, Stuttgart (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/171,717

(22) PCT Filed: Jan. 7, 1998

(86) PCT No.: PCT/DE98/00008

§ 371 (c)(1), (2), (4) Date: Apr. 8, 1999

(87) PCT Pub. No.: WO98/38505

PCT Pub. Date: Sep. 3, 1998

(30) Foreign Application Priority Data

Feb. 25, 1997 (DE) .......................................... 197 07 456

(51) Int. Cl.[7] .......................... G01N 27/12; H01C 7/00; G01M 19/00; H01L 7/00; B05D 5/12
(52) U.S. Cl. .................... 73/23.31; 73/23.32; 73/31.05; 338/34; 422/94; 123/672
(58) Field of Search .............................. 73/23.31, 23.32, 73/31.05, 31.06, 116; 422/98, 94; 338/34; 123/434, 672

(56) References Cited

U.S. PATENT DOCUMENTS

| 3,920,172 | A | | 11/1975 | Rhee ........................... 228/124 |
|---|---|---|---|---|
| 4,130,797 | A | * | 12/1978 | Hattori et al. .............. 324/65 P |
| 4,236,138 | A | * | 11/1980 | Segawa et al. ................ 338/34 |
| 4,308,518 | A | * | 12/1981 | Hattori et al. ................ 338/34 |
| 4,403,207 | A | * | 9/1983 | Murphy et al. ................ 338/34 |
| 4,414,531 | A | * | 11/1983 | Novak .......................... 338/34 |
| 4,665,740 | A | * | 5/1987 | Matsumoto et al. .......... 73/116 |
| 4,883,643 | A | * | 11/1989 | Nishio et al. .................. 422/94 |
| 4,958,514 | A | * | 9/1990 | Takami et al. ............. 73/25.03 |
| 5,039,972 | A | * | 8/1991 | Kato et al. ..................... 338/34 |
| 5,182,136 | A | * | 1/1993 | Saburi et al. ............. 427/126.3 |
| 5,228,975 | A | | 7/1993 | Yamada et al. ............. 204/424 |
| 5,329,806 | A | * | 7/1994 | McClanahan et al. ..... 73/31.05 |
| 5,467,636 | A | * | 11/1995 | Thompson et al. ........ 73/23.31 |
| 5,490,412 | A | * | 2/1996 | Duce et al. ................. 73/23.31 |

FOREIGN PATENT DOCUMENTS

EP 0 706 046 4/1996

* cited by examiner

*Primary Examiner*—Hezron Williams
*Assistant Examiner*—David J. Wiggins
(74) *Attorney, Agent, or Firm*—Kenyon & Kenyon

(57) ABSTRACT

A sensor for determining an oxygen content in an exhaust gas of an internal combustion engine includes a receptacle, arranged in a longitudinal bore of a metal housing, for a sensing element. The sensing element is received in the receptacle in a gas-tight fashion via a sensing element seal, which includes a glass seal. The receptacle has a measured-gas-side ceramic shaped element and a connector-side ceramic shaped element, which are arranged axially one behind the other. A cavity into which the glass seal is pressed while hot is configured between the two ceramic shaped elements.

16 Claims, 4 Drawing Sheets

SENSOR AND METHOD FOR THE MANUFACTURE

BACKGROUND INFORMATION

The present invention deletes to a sensor and a method for its manufacture U.S. Pat. No. 5,467,636 describes a known sensor in which a planar sensing element is immobilized in gas-tight fashion, by way of a sealing element, in a passthrough of an exhaust-gas-side lower ceramic shaped element. The exhaust-gas-side ceramic shaped element has on the end surface facing away from the exhaust gas a recess which surrounds the passthrough and into which a glass seal is introduced. A further ceramic shaped element, which is joined via a metal solder join to the housing, sits on the glass seal. The glass seal encloses the sensing element inside the recess, and constitutes a gas-tight join between ceramic shaped element and sensing element at this point.

SUMMARY OF THE INVENTION

The sensor according to the present invention has the advantage that a mechanically stable and gas-tight join is possible between the planar sensing element and both ceramic shaped elements.

The hermetic seal of the sensing element thereby achieved is vibration-proof, so that while the sensor is being used in the motor vehicle, the sensing element can be immobilized over the utilization period in a mechanically stable and hermetic fashion. The method according to the present invention makes it possible for gas-tight immobilization of the sensing element to be attained efficiently.

A particularly mechanically stable and gas-tight joining between the sensing element and the ceramic shaped elements is achieved if the glass seal covers the sensing element over as large an area as possible, but does not penetrate appreciably into the front region which is subject to high thermal stress when the sensor is later operated. The arrangement of a powdered additional seal on the measured-gas site in front of the glass seal prevents the molten glass from penetrating, during the melting process, into the front region of the sensing element that is subject to high thermal stress. It is advantageous for the manufacturing process that the two ceramic shaped elements are configured, on the end faces which face toward one another, in the form of a die and punch, and act accordingly on one another. This makes possible compression of the glass seal, and of the powdered additional seal that is optionally used, utilizing the geometry of the ceramic shaped elements. The presence of a gap between die and punch has the advantage that the glass seal can escape into the gap upon compression. This makes it possible to work with a high compressive force. At the same time, it prevents the two end faces of the ceramic shaped elements from striking one another. In addition, a further glass seal can be inserted into the annular gap between the ceramic shaped elements, or an annular metal foil or plate can be set in place, thus resulting in a positive joining between the two ceramic elements.

DETAILED DESCRIPTION

Figure 1:
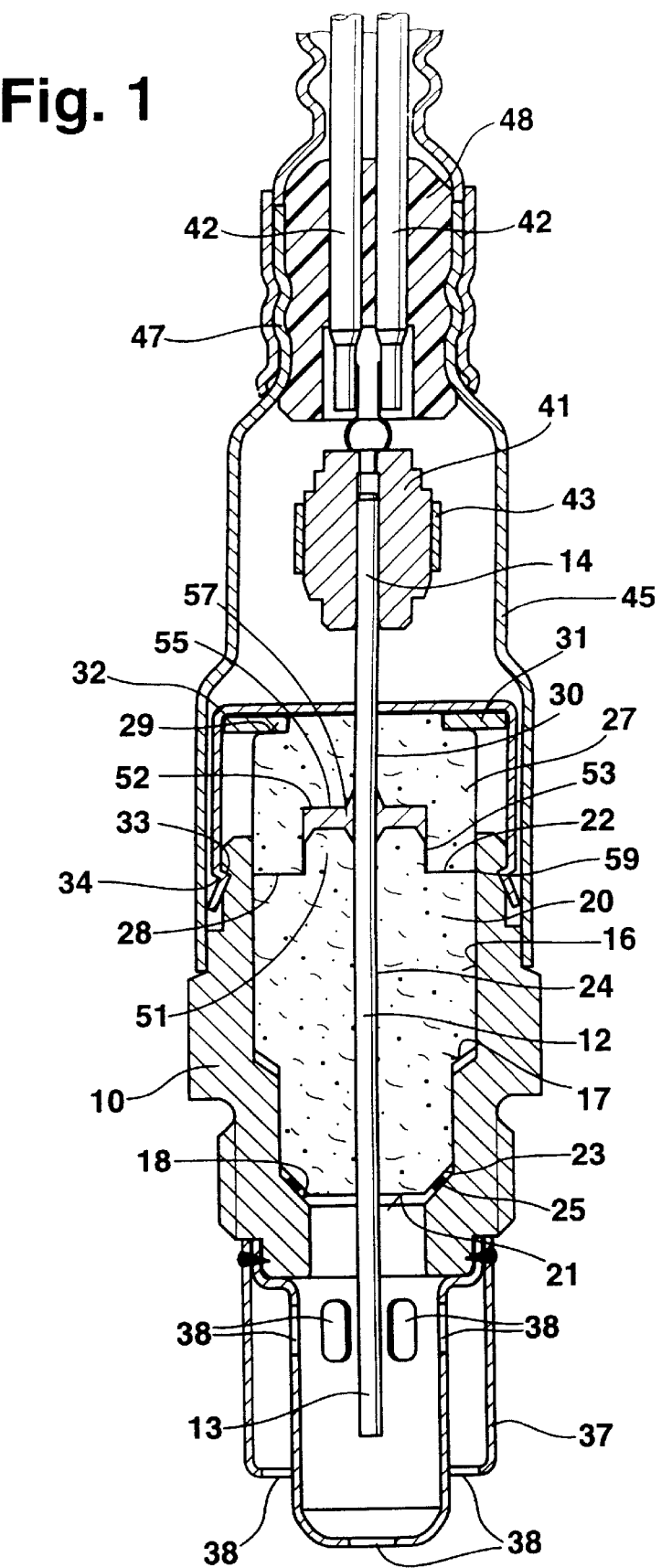
FIG. 1 shows a sectioned depiction through a sensor according to the present invention.

The sensor depicted in FIG. 1 is an electrochemical sensor for determining the oxygen content in exhaust gases of internal combustion engines. The sensor has a metal housing 10 in which a flat-plate sensing element 12, having a measured-gas-side end section 13 and a connector-side end section 14, is arranged. Housing 10 is configured with threads as attachment means for installation into an exhaust pipe (not depicted). Also arranged in housing 10 is a longitudinal bore 16 having, for example, a first shoulder-like annular surface 17 and a second shoulder-like annular surface 18.

Arranged in longitudinal bore 16 is a measured-gas-side ceramic shaped element 20 having a measured-gas-side passthrough 24, and having a measured-gas-side end face 21 and a connector-side end face 22. Measured-gas-side end face 21 is configured with a conically extending sealing seat 23 which sits on a metal sealing ring 25 that rests against second shoulder-like annular surface 18. Arranged above measured-gas-side ceramic shaped element 20 is a connector-side ceramic shaped element 27 having a connector-side passthrough 30 and having a measured-gas-side end face 28 and a connector-side end face 29.

A disk spring 31 that is under mechanical preload, which presses via a tubular retaining cap 32 onto measured-gas-side ceramic shaped element 20 that projects out of housing 10, rests on connector-side end face 29 of connector-side ceramic shaped element 27; retaining cap 32 engages via snap-lock tabs 34 into an annular groove 33 arranged on the outer side of housing 10. The two ceramic shaped elements 20, 27 are preloaded in the axial direction via retaining cap 32 and disk spring 31, so that measured-gas-side ceramic shaped element 20 presses with conical sealing seat 23 onto sealing ring 25. A gas-tight sealing seat thus forms between housing 10 and Measured-gas-side ceramic shaped element 20. Measured-gas-side end section 13 projecting out of the housing 10 is, for example, surrounded at a distance by a double-walled protective tube 37 having gas inlet and gas outlet openings 38. On connector-side end section 14, sensing element 12 has contacts (not depicted further) which make contact with connector cables 42 via a contact plug 41. Connector plug 41 includes, for example, two ceramic elements which are held together by a clamping piece 43. Connector-side end section 14 of sensing element 12, which projects out of connector-side ceramic shaped element 27, is surrounded by a metal sleeve 45 which is welded in gas-tight fashion to housing 10 and has a tubular opening 47 in which a cables passthrough 48 is located for the passage of connector cable 42.

Measured-gas-side ceramic shaped element 20 has on connector-side end face 22 a punch-shaped extension 51 which surrounds measured-gas-side passthrough 24. Connector-side ceramic shaped element 27 has on measured-gas-side end face 28 a recess 52 into which punch-shaped extension 51 penetrates with a radial gap 53. A cavity 55, which is filled with a glass seal 57, is formed between the end face of punch-shaped extension 51 and the bottom of recess 52. It is also possible to configure punch-shaped extension 51 on connector-side ceramic shaped element 27, and recess 52 on measured-gas-side ceramic shaped element 20.

Glass seal 57 causes sensing element 12 to be hermetically sealed in ceramic shaped elements 20, 27. The dimensions of punch-shaped extension 51 and of recess 52 are such that an annular gap 59 is formed between the mutually facing annular surfaces of measured-gas-side ceramic shaped element 20 and connector-side ceramic shaped element 27. The purpose of annular gap 59 is to allow the fusible glass of glass seal 57 to escape via radial gap 53 into annular gap 59 upon compression.

A fusible glass, for example a lithium aluminum silicate glass or a lithium barium aluminum silicate glass, is suitable as glass seal 57. Additives which improve the flow characteristics of the molten glass can be added to the fusible glass.

Powdered substances such as copper, aluminum, iron, brass, graphite, boron nitride, $MoS_2$, or a mixture of these substances, can be used as additives for plastification of glass seal 57 during the joining process. Lithium carbonate, lithium soap, borax, or boric acid are used, for example, as fluxes for glass seal 57. The addition of compensating fillers, such as aluminum nitride, silicon nitride, zirconium tungstate, or a mixture of these substances, is suitable for adjusting the thermal expansion. A further improvement in the joining between glass seal 57 and the ceramic of ceramic shaped elements 20, 27 is achieved if a ceramic binder, such as aluminum phosphate or chromium phosphate, is added to glass seal 57.

Figure 2:
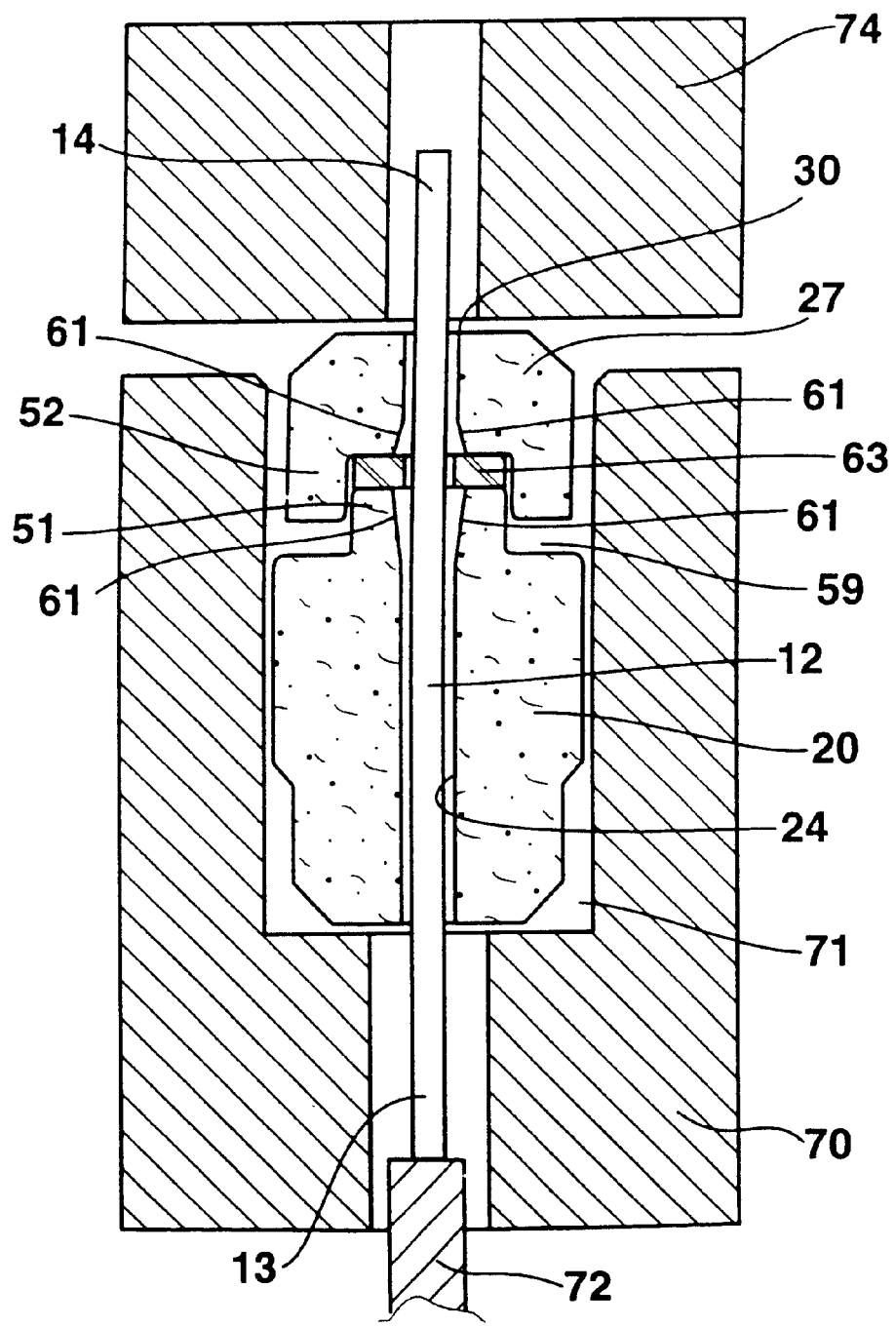
FIG. 2 shows a first exemplary embodiment according to the present invention of a sensing element seal for the sensing element in the uninstalled state, with an apparatus for manufacturing the seal.
Figure 3:
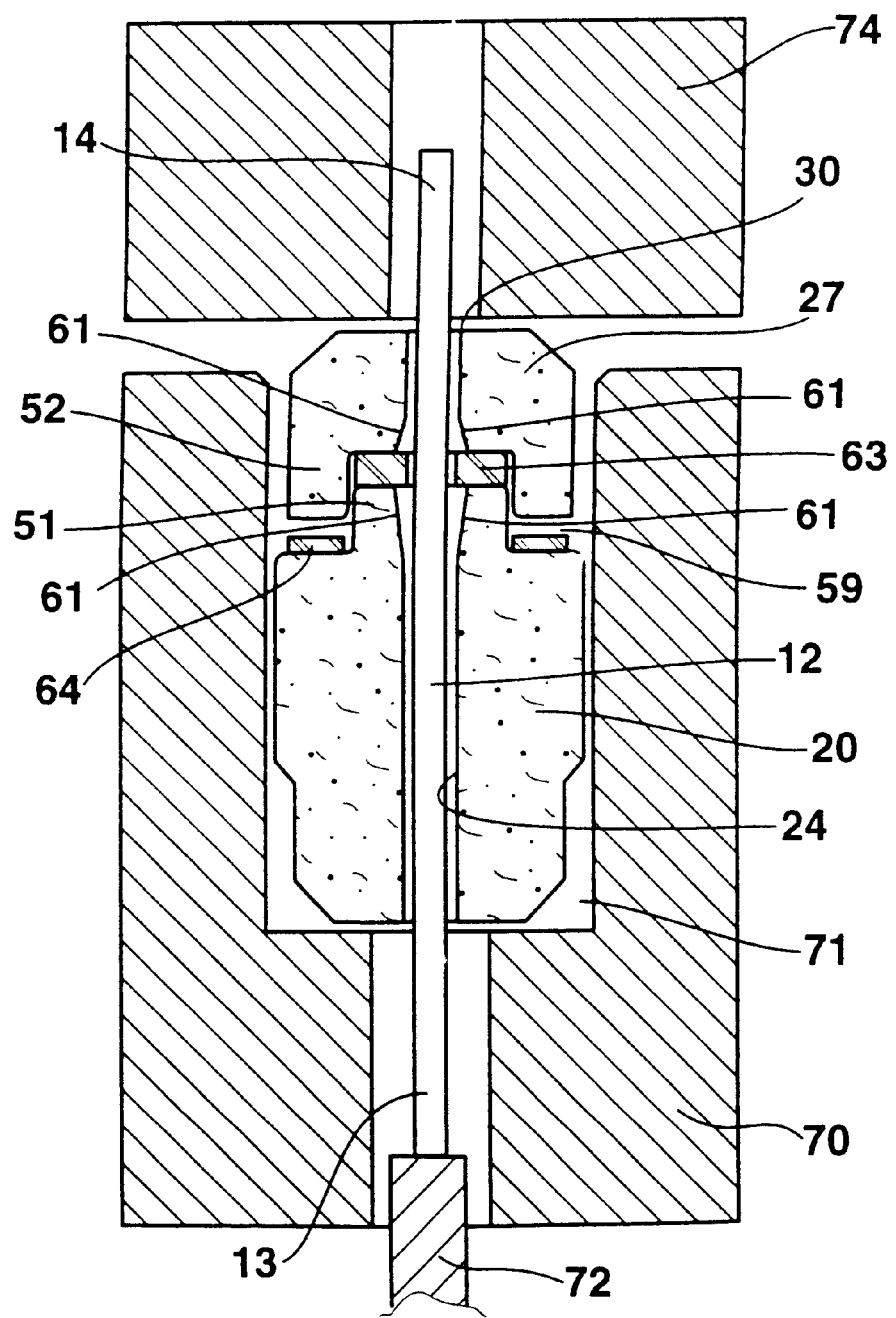
FIG. 3 shows a second exemplary embodiment according to the present invention of a sensing element seal in the uninstalled state.
Figure 4:
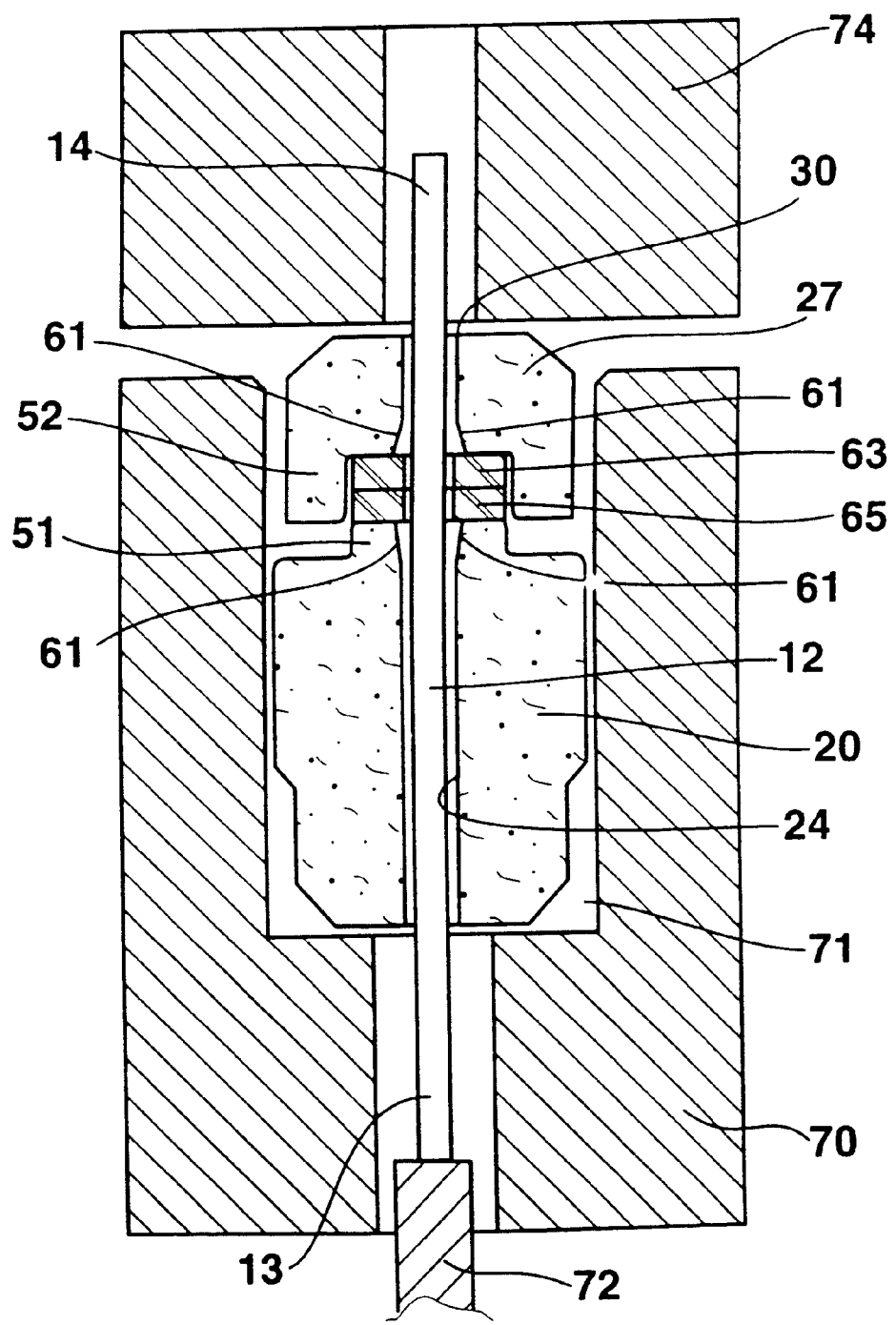
FIG. 4 shows a third exemplary embodiment according to the present invention of a sensing element seal in the uninstalled state.

In order to achieve large-area wetting of sensing element 12 with glass seal 57, in the present exemplary embodiments the side surfaces of measured-gas-side passthrough 24 and of connector-side passthrough 30 of ceramic shaped elements 20, 27 are each configured, toward cavity 55, with a conically extending enlargement 61 (FIGS. 2, 3, and 4).

Three exemplary embodiments of the sensing element seal in the uninstalled state, in each case with an apparatus for manufacturing glass seal 57, are evident from FIGS. 2, 3, and 4.

The apparatus has a support 70 acting as die, with a receptacle 71 and a stop 72. Ceramic shaped elements 20 and 27 are positioned in receptacle 71 with sensing element 12 received in passthroughs 24, 30. The axial position of sensing element 12 is defined in this context by stop 72, sensing element 12 resting with measured-gas-side end section 13 on stop 72. Measured-gas-side ceramic shaped element 20 is first inserted with sensing element 12 into receptacle 71. A glass blank 63, for example in the form of a glass pellet or glass film, is placed onto the end surface of punch-shaped extension 51, glass blank 63 having an opening with which glass blank 63 is slid over sensing element 12. Connector-side ceramic shaped element 27 is then placed onto glass blank 63, so that connector-side end section 14 of sensing element 12 projects through passthrough 30. In the arrangement described, a compressive force of, for example, 600 kg-force (Kilogram Force) is applied onto connector-side ceramic shaped element 27 using a pressing punch 74. Beforehand, however, glass blank 63 was heated, for example by a heating device housed in support 70, to a temperature above the softening temperature of the fusible glass or glass ceramic being used. Upon compression, the fluid glass blank 63 deforms and is thereby pressed into conical enlargements 61 and into radial gap 53. Fusible glass flowing out via radial gap 59 can escape into end-surface annular gap 53.

A second exemplary embodiment is depicted in FIG. 3. This exemplary embodiment differs from the exemplary embodiment of FIG. 1 in that a further annular glass blank 64 is inserted into annular gap 59. Upon compression, the fluid glass blank 64, like glass blank 63, deforms so that annular gap 59 is additionally sealed with a further glass seal.

A further exemplary embodiment of a sensing element seal is evident from the arrangement in FIG. 4. Here a further blank 65, precompressed and optionally presintered, is arranged on the measured-gas side below glass blank 63. Materials with good plastic deformability, such as talc, kaolin, clay, bentonite, graphite, boron nitride, etc. are in principle particularly suitable as the material for blank 65. As punch 74 is applied during compression of the fluid glass blank 63, blank 65 is simultaneously deformed into its powder constituents, thus resulting in a powdered additional seal. Before the fusible glass flows in, the powder penetrates into the gap of measured-gas-side passthrough 24 formed by conical enlargement 61, so that the fusible glass is prevented from flowing to the measured-gas end of ceramic shaped element 20 that is subject to high thermal stress.

The apparati depicted in FIGS. 3 and 4 correspond to the apparatus of FIG. 2. The method for manufacturing glass seal 57 according to FIG. 4 can be carried out in accordance with the method implemented using the apparatus in FIG. 2. It is also possible, however, first to deform blank 65 into powder using a punch and press it into the gap between sensing element 12 and measured-gas-side passthrough, 24 and then to compress glass blank 63 using the procedure according to FIG. 2. A further embodiment of the sensing element seal according to FIG. 4, having a further fused glass seal in annular gap 59 as in the case of the exemplary embodiment in FIG. 3, is also possible.

What is claimed is:

1. A sensor for determining an oxygen content in an exhaust gas of an internal combustion engine, comprising:

a metal housing having a longitudinal bore;

a receptacle situated in the longitudinal bore of the metal housing and including a measured-gas-side ceramic shaped element and a connector-side ceramic shaped element, the measured gas-side ceramic shaped element having an extension that cooperates with a recess formed in the connector-side ceramic shaped element to form a cavity and a closeable radial gap;

a sensing element seal including a glass seal that is pressed while molten into the cavity; and a sensing element situated in the receptacle in a gas-tight manner via the sensing element seal.

2. The sensor according to claim 1, wherein:

the measured-gas-side ceramic shaped element and the connector-side ceramic shaped element are arranged axially adjacent to each other, the measured-gas-side ceramic shaped element includes a punch-shaped extension, the connector-side ceramic shaped element includes a recess, and the cavity is formed in the recess.

3. The sensor according to claim 2, wherein:

the punch-shaped extension is formed on the measured-gas-side ceramic shaped element, and the recess is formed on the connector-side ceramic shaped element.

4. The sensor according to claim 2, wherein the punch-shaped extension extends into the recess and is surrounded by a radial gap.

5. The sensor according to claim 1, wherein the glass seal includes one of a lithium aluminum silicate glass and a lithium barium aluminum silicate glass.

6. The sensor according to claim 1, wherein the glass seal includes a plurality of additives including one of a plurality of plasticizers, a plurality of fluxing agents, a plurality of fillers, and a mixture of at least two of the plurality of plasticizers, the plurality of fluxing agents, and the plurality of fillers.

7. The sensor according to claim 6, wherein the plurality of plasticizers include one of copper, aluminum, iron, brass, graphite, boron nitride, $MoS_2$, and a mixture of at least two of copper, aluminum, iron, brass, graphite, boron nitride, and $MoS_2$.

8. The sensor according to claim 1, wherein:
the measured-gas-side ceramic shaped element includes a first axially extending passthrough,
the connector-side ceramic shaped element includes a second axially extending passthrough, and
at least one of the first axially extending passthrough and the second axially extending passthrough includes an expansion region facing the cavity.

9. The sensor according to claim 1, wherein the sensing element seal includes at least one powdered sealing packing provided at least on the measured-gas-side ceramic shaped element.

10. The sensor according to claim 9, wherein the at least one powdered sealing packing is situated in the cavity adjacent to the glass seal on a side of the sensing element that is subject to a predetermined thermal stress.

11. The sensor according to claim 10, wherein the at least one powdered sealing packing is formed of a ceramic.

12. The sensor according to claim 9, wherein the at least one powdered sealing packing is formed of one of steatite, graphite, boron nitride, $Al_2O_3$, $ZrO_2$, and a mixture of one of steatite, graphite, boron nitride, $Al_2O_3$, and $ZrO_2$.

13. An electrochemical sensor for determining an oxygen content in an exhaust gas of an internal combustion engine, comprising:

an axially extending sensing element having an axial length; and
a seal surrounding the sensing element over a portion of the axial length, the seal hermetically sealing the sensing element in a radial direction and being vibration-proof in an axial direction, the seal including:
a first ceramic shaped element having a recess;
a second ceramic shaped element having an extension, the extension cooperating with the recess, forming a cavity and a closeable radial gap, the cavity being filled with a pressed-in molten glass seal.

14. The electrochemical sensor of claim 13 wherein the sensing element is a flat plate solid electrolyte.

15. The electrochemical sensor of claim 13, wherein the seal further includes
a spring, the spring causing the one of the first and second shaped elements to exert pressure on the further ceramic shaped element; and
a sealing element, the sealing element creating a hermetic seal and preventing axial movement of both ceramic shaped elements in response to the pressure exerted on one of the first and second shaped elements.

16. A sealing element for an sealing an axially extending sensing element in an electrochemical gas sensor, comprising:
a first ceramic shaped element having a recess;
a second ceramic shaped element having an extension, the extension cooperating with the recess, a cavity and a closeable radial gap being bounded by the first and second cooperating ceramic shaped elements; and
a glass seal formed from pressed-in molten glass within the cavity.

\* \* \* \* \*

UNITED STATES PATENT AND TRADEMARK OFFICE
CERTIFICATE OF CORRECTION

PATENT NO.    : 6,408,680 B2
DATED         : June 25, 2002
INVENTOR(S)   : Friese et al.

It is certified that error appears in the above-identified patent and that said Letters Patent is hereby corrected as shown below:

Column 1,
Line 5, change "deletes" to -- relates --;

Column 2,
Line 52, change "cables" to -- cable --;
Line 53, change "cable" to -- cables --;

Column 3,
Line 59, change "59" to -- 53 --;
Line 60, change "53" to -- 59 --;

Column 4,
Line 22, change "passthrough, 24" to -- passthrough 24, --.

Signed and Sealed this

Fourth Day of May, 2004

JON W. DUDAS
*Acting Director of the United States Patent and Trademark Office*